(12) United States Patent
Kalvinsh et al.

(10) Patent No.: US 8,846,944 B2
(45) Date of Patent: Sep. 30, 2014

(54) REGENERATION OF 2,2'-CYCLOPROPYLIDENE-BIS (OXAZOLINES)

(75) Inventors: Ivars Kalvinsh, Ikshkile (LV); Antons Lebedevs, Riga (LV); Aleksandrs Chernobrovijs, Riga (LV); Grigory Veinberg, Riga (LV); Maksims Vorona, Riga (LV); Agnija Ievina, Riga (LV)

(73) Assignee: Latvian Institute of Organic Synthesis, Riga (LV)

( * ) Notice: Subject to any disclaimer, the term of this patent is extended or adjusted under 35 U.S.C. 154(b) by 356 days.

(21) Appl. No.: 12/998,818

(22) PCT Filed: Nov. 30, 2009

(86) PCT No.: PCT/IB2009/055413
§ 371 (c)(1),
(2), (4) Date: Jul. 11, 2011

(87) PCT Pub. No.: WO2010/064189
PCT Pub. Date: Jun. 10, 2010

(65) Prior Publication Data
US 2011/0263864 A1    Oct. 27, 2011

(30) Foreign Application Priority Data
Dec. 3, 2008 (LV) ..................... P-08-199

(51) Int. Cl.
*C07D 263/62* (2006.01)

(52) U.S. Cl.
CPC .................. *C07D 263/62* (2013.01)
USPC .......................... 548/219; 548/238

(58) Field of Classification Search
None
See application file for complete search history.

(56) References Cited

U.S. PATENT DOCUMENTS 5,298,623 A * 3/1994 Masamune et al. ........... 548/101

\* cited by examiner

*Primary Examiner* — Alicia L Otton
(74) *Attorney, Agent, or Firm* — Colin P. Abrahams

(57) ABSTRACT

The present invention provides a method for regeneration of chiral 2,2'-cyclopropylidene-bis(oxazolines), such as (3&R, 3'aR,8aS,8'aS)-2,2'-cyclopropylidenebis-[3a,8a]-dihydro-8H-indeno-[1,2-d]-oxazole and (45,4'5,5R,5'R)-2,2'-cyclopropylidenebis-4,5-diphenyldihydro-4,5-oxazole, used as a part of complex catalysts for e.g. stereoselective addition reactions, from the reaction mixtures, by selective sorption of 2,2'-cyclopropylidene-bis(oxazolines) on a sorbent, such as silica gel, isolation of the sorbent from reaction mixture, desorption of 2,2'-cyclopropylidene-bis(oxazolines) from the sorbent with suitable organic solvent and final recovery of 2,2'-cyclopropylidene-bis(oxazolines) from the organic solvent used for desorption process. Catalytic quality of recovered compounds does not differ from those in freshly prepared catalysts.

12 Claims, No Drawings

REGENERATION OF 2,2'-CYCLOPROPYLIDENE-BIS (OXAZOLINES)

TECHNICAL FIELD

The invention relates to the regeneration and multiple usage of chiral 2,2'-cyclopropylidene-bis(oxazolines), which represent the ligand part of complex catalyst widely used in stereoselective synthesis.

BACKGROUND ART

Generally, chiral $C_2$-bis(oxazolines) are known to serve as successful ligands in several catalytic processes, including Diels-Alder, aldol, aziridination, allylic alkylation and cyclopropanation reactions. Complex catalysts consisting of conjugate between chiral 2,2'-cyclopropylidene-bis-oxazoles and magnesium triflate in combination with amine provides addition of ketoesters or malonates to nitroolefins with excellent enantioselectivity (e.g., Ji J., et al., *J. Am. Chem. Soc.*, 1999, 121, 10215, and Barnes D. M., et al., *J. Am. Chem. Soc.*, 2002, 124, 13097). Nichols P., et al. in WO2004096764 patent application discloses a method of preparing ring compounds with chiral centers in the presence of a catalyst complex comprising bis(oxazolines) as a ligand.

At the same time, application of this methods for large-scale production of asymmetric organic compounds is problematic from economical point of view, mainly due to the employment of expensive chiral bis(oxazolines) in technological process as disposable material. Previous attempts to develop a method for recovery of that valuable catalyst in such reactions include immobilization of the bis(oxazoline) catalyst on organic and inorganic polymers, ion-pairing with an anionic support and covalent attachment to silica. Examples of regeneration of insoluble polymer-bound bis (oxazolines) were described, e.g., polystyrene-bound, as showed by P. Salvadori et al., *Tetrahedron: Asymmetry*, 2004, 15, 3233, and grafted on ArgoGel, as shown by C. Moberg et al., *Tetrahedron: Asymmetry*, 2001, 12, 1475. A number of sources describe the use of ionic liquids and anionic solids to obtain recoverable catalysts for reactions promoted by cationic chiral bis(oxazoline) complexes (e.g. J. A. Mayoral et al., *Green Chem.*, 2004, 6, 93 and D. L. Davies et al., *Tetrahedron: Asymmetry*, 2004, 15, 77). Additionally, J. A. Mayoral et al. presented immobilization of bis(oxazolines) by functionalization of the central methylene bridge with polymerizable organic groups and subsequent polymerization (*Org. Lett.*, 2000, 2, 3905) and grafting bis(oxazolines) functionalized with two allyl or vinylbenzyl groups onto mercaptopropylsilica (*J. Org. Chem.*, 2001, 66 (26), 8893).

One example is known for 4-naphthyl-substituted bis(oxazoline) ligand to be recovered from reaction mixture by a simple filtration due to its low solubility in polar solvents (G. Desimoni et al., *Tetrahedron*, 1998, 51, 15721).

Summarizing the entire above-mentioned prior art, except of the very last one, it should be underlined that immobilization of chiral bis(oxazoline) catalysts has substantial disadvantages. Usually, the type of immobilization modifies the catalytic performance and, in particular, the enantioselectivity. In most cases immobilization requires chemical modification of the ligand with changes in its activity and selectivity. In some cases polymer was reported to inhibit the entire reaction. Enantioselectivity issues were discussed also in case of ionic liquids, where crucial role plays the stability of the catalyst complex (when the complex is not so stable, the equilibrium between the complexed and free form of the metal may lead to the presence of nonchiral sites, with the consequent reduction in enantioselectivity), purity of the ionic liquid, its dryness and synthetic method used or preparation of the ionic liquid. Moreover, some of recovery procedures of the immobilized catalyst are likely not to be translated to an industrial scale due to particular specific steps (e.g. use of saturated solution of KCN in DMSO as by C. Moberg et al., *Tetrahedron: Asymmetry*, 2001, 12, 1475).

The above-mentioned recovery of 4-naphthyl-substituted bis(oxazoline) ligand from reaction mixture by filtration due to its low solubility in polar solvents is a standalone example which characterizes that particular ligand and cannot be considered as a general procedure.

Thus, no universal method, easily scaled to industrial application, was describes so far, providing selective isolation of bis(oxazolines) per se from homogeneous solutions and their multiple usage for catalytic purposes.

Obviously, development of easy and effective method for isolation of chiral 2,2'-cyclopropylidene-bis(oxazolines) from the homogeneous reaction mixture for a multiple usage is highly desirable and potentially of a significant positive economical effect. Effective isolation of chiral 2,2'-cyclopropylidene-bis(oxazolines) from reaction mixture and its repeated re-use in synthetic procedure could significantly improve both technological and economical characteristics of the large-scale production of desired asymmetric products.

The present invention overcomes disadvantages of the recovery methods known up to date and provides for a simple and effective method of regeneration of chiral 2,2'-cyclopropylidene-bis(oxazolines) from reaction mixtures, as described further, without loss in catalytic quality.

DISCLOSURE OF INVENTION

The present invention relates to the regeneration from reaction mixtures and multiple usage of chiral 2,2'-cyclopropylidene-bis(oxazolines), which represent the ligand part of complex catalyst widely used e.g. for stereoselective addition of enolates to nitroalkens. According to the present invention, chiral 2,2'-cyclopropylidene-bis(oxazolines) could be effectively recovered directly or indirectly from reaction mixtures in which they are contained, by sorption on available non-expensive sorbent, preferably on silica gel, while changing the polarity of solvents.

According to the present invention, preferred ligands from bridged bis(oxazoline) family are represented with (3aR, 3'aR,8aS,8'aS)-2,2'-cyclopropylidenebis-[3a,8a]-dihydro-8H-indeno-[1,2-d]-oxazole (1) and (4S,4'S,5R,5'R)-2,2'-cyclopropylidenebis-4,5-diphenyldihydro-4,5-oxazole (2).

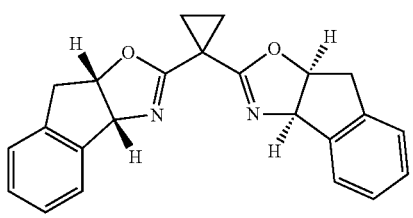

1

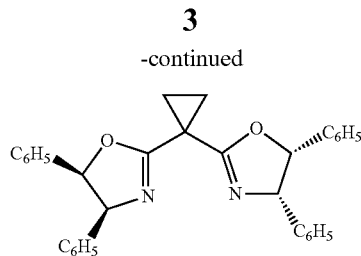

In one aspect, the present invention provides a direct method for regeneration of chiral 2,2'-cyclopropylidene-bis(oxazolines) from the reaction mixture comprising the following steps of:

(a) providing a reaction mixture, containing chiral 2,2'-cyclopropylidene-bis(oxazoline);

(b) sorption of chiral 2,2'-cyclopropylidene-bis(oxazoline) from a reaction mixture of the previous step using silica gel;

(c) separation of the silica gel with sorbed chiral 2,2'-cyclopropylidene-bis(oxazoline) from a reaction mixture;

(d) desorption of chiral 2,2'-cyclopropylidene-bis(oxazoline) from silica gel using organic solvent;

(e) recovery of chiral 2,2'-cyclopropylidene-bis(oxazoline) from organic solvent.

In the preferred embodiment, solvents of the reaction mixture in the step (a) above are selected from the group consisting, but not limited to hexane, benzene, toluene, chloroform, dichloromethane, dichloroethane, diethyl ether, methyl t-butyl ether and their mixtures.

Separation of the silica gel with sorbed chiral 2,2'-cyclopropylidene-bis(oxazolines) from a reaction mixture (step (c) in the description above) can be accomplished using any suitable method known in the art, e.g. by filtration.

In the preferred embodiment, desorption of chiral 2,2'-cyclopropylidene-bis(oxazolines) from silica gel (step (d) in the description above) can be accomplished using solvents, selected from the group consisting, but not limited to methanol, ethanol, n-propanol, isopropanol, acetone, acetonitrile, tetrahydrofuran, 1,4-dioxane and their mixtures.

Recovery of chiral 2,2'-cyclopropylidene-bis(oxazolines) from organic solvent used for desorption procedure (step (e) in the description above) can be accomplished using any suitable method known in the art, preferably by crystallization or by the solvent evaporation under reduced pressure.

In another aspect, the present invention provides an indirect method for regeneration of chiral 2,2'-cyclopropylidene-bis(oxazolines) from the reaction mixture comprising the following steps of:

(a) providing a reaction mixture, containing chiral 2,2'-cyclopropylidene-bis(oxazoline);

(b) evaporation of solvent from reaction mixture of the previous step under reduced pressure, obtaining a residue;

(c) dissolution of the residue of the previous step in organic solvent;

(d) sorption of chiral 2,2'-cyclopropylidene-bis(oxazoline) from the obtained solution using silica gel;

(e) separation of the silica gel with sorbed chiral 2,2'-cyclopropylidene-bis(oxazoline) from a solution;

(f) desorption of chiral 2,2'-cyclopropylidene-bis(oxazoline) from silica gel using organic solvent;

(g) recovery of chiral 2,2'-cyclopropylidene-bis(oxazoline) from organic solvent.

In the preferred embodiment, solvents for the step (c) in the description above are selected from the group consisting, but not limited to hexane, benzene, toluene, chloroform, dichloromethane, dichloroethane, diethyl ether, methyl t-butyl ether and their mixtures.

Separation of the silica gel with sorbed chiral 2,2'-cyclopropylidene-bis(oxazolines) from a reaction mixture (step (e) in the description above) can be accomplished using any suitable method known in the art, e.g. by filtration.

In the preferred embodiment, desorption of chiral 2,2'-cyclopropylidene-bis(oxazolines) from silica gel (step (f) in the description above) can be accomplished using solvents, selected from the group consisting, but not limited to methanol, ethanol, n-propanol, isopropanol, acetone, acetonitrile, tetrahydrofuran, 1,4-dioxane and their mixtures.

Recovery of chiral 2,2'-cyclopropylidene-bis(oxazolines) from organic solvent used for desorption procedure (step (g) in the description above) can be accomplished using any suitable method known in the art, preferably by crystallization or by the solvent evaporation under reduced pressure.

According to the current invention, reaction mixtures where chiral 2,2'-cyclopropylidene-bis(oxazolines) are recovered from, may contain also other components of a catalyst complex, as well as other reaction starting and/or end products and/or intermediates, molecular sieves and appropriate organic solvents.

According to the current invention, both direct and indirect methods for recovery of chiral 2,2'-cyclopropylidene-bis(oxazolines) are applicable to addition reactions of ketoesters or malonates to nitroolefins.

According to the current invention, and as supported by further examples, catalytic quality of recovered 2,2'-cyclopropylidene-bis(oxazolines) does not differ from that in freshly prepared catalyst.

Thus, the present invention provides convenient and effective methods for both direct and indirect regeneration of chiral 2,2'-cyclopropylidene-bis(oxazolines) from the reaction mixtures, where these compounds are used as a part of a complex catalysts.

The scope of the invention should not be limited to the working examples, which are for demonstration purposes. One skilled in the art can practice the invention based on the disclosures in the present patent application.

EXAMPLES

The following examples are illustrating but not restricting the present invention.

Example 1

Step A. Silica gel (100 g) was added to reaction mixture after the completion of the Michael addition of diethyl malonate (70.42 g, 0.44 mol) to 2-nitrovinylbenzene (59.6 g, 0.40 mol) in chloroform (2.01) catalyzed by catalyst complex consisting of (3aR,3'aR,8aS,8'aS)-2,2'-cyclopropylidenebis-[3a,8a]-dihydro-8H-indeno-[1,2-d]-oxazole (8.55 g, 24 mmol), magnesium triflate (6.4 g, 20 mmol) and N-methylmorpholine (2.6 g, 26.4 mmol) in the presence of molecular sieves 4 Å (70 g).

Step B. Obtained suspension was stirred for 2 hours at 20-25° C. Silica gel was filtered off* and washed with ethanol 2×250 ml. Ethanol solution was partially evaporated under reduced pressure giving 8.03 g (94%) of recovered crystalline (3aR, 3'aR,8aS,8'aS)-2,2'-cyclopropylidenebis-[3a,8a]-dihydro-8H-indeno-[1,2-d]-oxazole.

*Standard treatment of chloroform filtrate obtained after separation of silica gel resulted in the isolation of diethyl 2-(2-nitro-1R-phenylethyl)malonate (111.4 g 90%; ee 98-99%).

Example 2

Step A. Silica gel (100 g) was added to reaction mixture after the completion of the Michael addition of diethyl malonate (70.42 g, 0.44 mol) to 2-nitrovinylbenzene (59.6 g, 0.40 mol) in chloroform (2.01) catalyzed by catalyst complex consisting of (4S,4'S,5R,5'R)-2,2'-cyclopropylidenebis-4,5-diphenyldihydro-4,5-oxazole (11.63 g, 24 mmol), magnesium triflate (6.4 g, 20 mmol) and N-methylmorpholine (2.6 g, 26.4 mmol) in the presence of molecular sieves 4 Å (70 g).

Step B. Obtained suspension was stirred for 2 hours at 20-25° C. Silica gel was filtered off* and washed with ethanol 2×250 ml. Ethanol solution was partially evaporated under reduced pressure giving 10.98 g (94%) of recovered crystalline (4S,4'S,5R,5'R)-2,2'-cyclopropylidenebis-4,5-diphenyldihydro-4,5-oxazole.

*Standard treatment of chloroform filtrate obtained after separation of silica gel resulted in the isolation of diethyl 2-(2-nitro-1R-phenylethyl)malonate (108.5 g 87%; ee 98-99%).

Example 3

Step A. Silica gel (10 g) was added to reaction mixture after the completion of the Michael addition of ethyl acetoacetate (1.56 g, 12 mmol) to 2-nitrovinylbenzene (1.64 g, 11 mmol) in chloroform (60 ml) catalyzed by catalyst complex consisting of (3aR, 3'aR,8aS,8'aS)-2,2'-cyclopropylidenebis-[3a,8a]-dihydro-8H-indeno-[1,2-d]-oxazole (240 mg, 0.67 mmol), magnesium triflate (170 mg, 0.5 mmol) and N-methylmorpholine (80 mkl, 0.72 mmol) in the presence of molecular sieves 4 Å (2.0 g).

Step B. Obtained suspension was stirred for 2 hours at 20-25° C. Silica gel was filtered off*, placed on the top of chromatographic column filled with 20 g of fresh silica gel and eluted with dichloromethane-methanol mixture 20:1. Fractions with $R_f$ 0.48 were collected and evaporated under reduced pressure giving 228 mg (95%) of recovered crystalline (3aR,3'aR,8aS,8'aS)-2,2'-cyclopropylidenebis-[3a,8a]-dihydro-8H-indeno-[1,2-d]-oxazole.

*Standard treatment of chloroform filtrate obtained after separation of silica gel resulted in the isolation of ethyl 2-acetyl-4-nitro-3R-phenylbutyrate (2.86 g 93%; 89% ee).

Example 4

In example 3, the substitution of (3aR,3'aR,8aS,8'aS)-2,2'-cyclopropylidenebis-[3a,8a]-dihydro-8H-indeno-[1,2-d]-oxazole with (4S,4'S,5R,5'R)-2,2'-cyclopropylidenebis-4,5-diphenyldihydro-4,5-oxazole resulted in the preparation of ethyl 2-acetyl-4-nitro-3R-phenylbutyrate with 91% yield and 88% ee, and 95% of (4S,4'S,5R,5'R)-2,2'-cyclopropylidenebis-4,5-diphenyldihydro-4,5-oxazole were successfully recovered.

Example 5

The substitution of chloroform in example 1 and 2 (Step A) by the same volume of dichloromethane resulted in 87-90% recovery of each catalyst.

Example 6

The substitution of chloroform in example 1 and 2 (Step A) by the same volume of dichloroethane resulted in 84-87% recovery of each catalyst.

Example 7

The substitution of chloroform in example 1 and 2 (Step A) by the same volume of benzene resulted in 89-91% recovery of each catalyst.

Example 8

The substitution of chloroform in example 1 and 2 (Step A) by the same volume of toluene resulted in 90-93% recovery of each catalyst.

Example 9

The substitution of chloroform in example 1 and 2 (Step A) by the same volume of methyl t-butyl ether resulted in 85-87% recovery of each catalyst.

Example 10

The substitution of chloroform in example 1 and 2 (Step A) by the same volume of hexane-ethyl acetate mixture (3:1) resulted in 87-91% recovery of each catalyst.

Example 11

The substitution of ethanol in example 1 and 2 (Step B) by methanol resulted in 90-93% recovery of each catalyst.

Example 12

The substitution of ethanol in example 1 and 2 (Step B) by acetone resulted in 88-93% recovery of each catalyst.

Example 13

The substitution of ethanol in example 1 and 2 (Step B) by n-propanol resulted in 88-93% recovery of each catalyst.

Example 14

The substitution of ethanol in example 1 and 2 (Step B) by isopropanol resulted in 88-93% recovery of each catalyst.

Example 15

The substitution of ethanol in example 1 and 2 (Step B) by methylethylketone resulted in 86-90% recovery of each catalyst.

Example 16

The substitution of ethanol in example 1 and 2 (Stage B) by acetonitrile resulted in 86-90% recovery of each catalyst.

Example 17

The substitution of ethanol in example 1 and 2 (Stage B) by tetrahydrofuran resulted in 86-90% recovery of each catalyst.

Example 18

The substitution of ethanol in example 1 and 2 (Step B) by 1,4-dioxane resulted in 86-90% recovery of each catalyst.

Example 19

Step A. The reaction mixture after the completion of the Michael addition of diethyl malonate to 2-nitrovinylbenzene in ethyl acetate (2.01) according to Example 1 was filtrated and evaporated under reduced pressure and the residue was re-dissolved in chloroform (2.01).

Step B. Silica gel (100 g) was added to chloroform solution and obtained suspension was stirred for 2 hours at 20-25° C.

Silica gel was filtered off and washed with ethanol 2×250 ml. Obtained solution was partially evaporated under reduced pressure giving 7.87 g (92%) of recovered crystalline (3aR, 3'aR,8aS,8'aS)-2,2'-cyclopropylidenebis-[3a,8a]-dihydro-8H-indeno-[1,2-d]-oxazole.

Example 20

Step A. The reaction mixture after the completion of the Michael addition of diethyl malonate to 2-nitrovinilbenzene in ethyl acetate (2.01) according to Example 2 was filtrated and evaporated under reduced pressure and the residue was re-dissolved in chloroform (1.01).

Step B. Silica gel (100 g) was added to chloroform solution and obtained suspension was stirred for 2 hours at 20-25° C. Silica gel was filtered off and washed with chloroform (2×200 ml) and then with ethanol 2×250 ml. Obtained solution was partially evaporated under reduced pressure giving 10.58 g (91%) of recovered crystalline (4S,4'S,5R,5'R)-2,2'-cyclopropylidenebis-4,5-diphenyldihydro-4,5-oxazole.

Example 21

The same procedure as in example 1 above, but performed with recovered catalyst. Components load was, accordingly:
2-Nitrovinylbenzene—0.164 g (1.1 mmol)
Diethyl malonate—0.195 g (0.18 ml, 1.22 mmol)
(3aR,3'aR,8aS,8'aS)-2,2'-cyclopropylidenebis-[3a,8a]-dihydro-8H-indeno-[1,2-d]-oxazole—24 mg (0.067 mmol)
$Mg(OTf)_2$—17 mg (0.05 mmol)
N-Methylmorpholine—7 mg (8 mkl, 0.072 mmol)
Molecular sieves—0.19 g
Chloroform—6 ml
Yield of the diethyl 2-(2-nitro-1R-phenylethyl)malonate: 275 mg (80.8%), optical purity: 99.3% ee.

The invention claimed is:

1. A process for regeneration of chiral 2,2'-cyclopropylidene-bis(oxazoline) from a reaction mixture of a catalytic organic reaction, in which said 2,2'-cyclopropylidene-bis(oxazoline) is used as ligand part of a complex catalyst, comprising the following steps of: separation of 2,2'-cyclopropylidene-bis(oxazoline) from the reaction mixture by sorption of 2,2'-cyclopropylidene-bis(oxazoline) on a sorbent; isolation of the sorbent with sorbed 2,2'-cyclopropylidene-bis(oxazoline) from reaction mixture; desorption of 2,2'-cyclopropylidene-bis(oxazoline) from the sorbent; recovery of 2,2'-cyclopropylidene-bis(oxazoline) from organic solvent used for desorption procedure, and the 2,2'-cyclopropylidene-bis(oxazoline) is (3aR,3'aR,8aS,8'aS)-2,2'-cyclopropylidenebis-[3a,8a]-dihydro-8H-indeno-[1,2-d]-oxazole.

2. A process according to claim 1, wherein the reaction is a stereo selective addition of ketoesters to nitroolefins.

3. A process according to claim 1, wherein the reaction is a stereoselective addition of malonates to nitroolefins.

4. A process according to claim 1, wherein organic solvent of the reaction mixture of step (1) containing 2,2'-cyclopropylidene-bis(oxazoline) is selected from the group, consisting of hexane, benzene, toluene, chloroform, dichloromethane, dichloroethane, diethyl ether, methyl t-butyl ether and their mixtures.

5. A process according to claim 1, wherein the sorbent is silica gel.

6. A process according to claim 1, wherein for desorption an organic solvent is used, selected from the group, consisting of methanol, ethanol, n-propanol, isopropanol, acetone, methylethylketone, acetonitrile, tetrahydrofuran, 1,4-dioxane and their mixtures.

7. A process for regeneration of chiral 2,2'-cyclopropylidene-bis(oxazoline) from a reaction mixture of a catalytic organic reaction, in which said 2,2'-cyclopropylidene-bis(oxazoline) is used as ligand part of a complex catalyst, comprising the following steps of: separation of 2,2'-cyclopropylidene-bis(oxazoline) from the reaction mixture by sorption of 2,2'-cyclopropylidene-bis(oxazoline) on a sorbent; isolation of the sorbent with sorbed 2,2'-cyclopropylidene-bis(oxazoline) from reaction mixture; desorption of 2,2'-cyclopropylidene-bis(oxazoline) from the sorbent; recovery of 2,2'-cyclopropylidene-bis(oxazoline) from organic solvent used for desorption procedure, and the 2,2'-cyclopropylidene-bis(oxazoline) is selected from the group consisting of (3aR, 3'aR,8aS,8'aS)-2,2'-cyclopropylidenebis-[3a,8a]-dihydro-8H-indeno-[1,2-d]-oxazole and (4S,4'S,5R,5'R)-2,2'-cyclopropylidenebis-4,5-diphenyldihydro-4,5-oxazole.

8. A process according to claim 7, wherein the reaction is a stereo selective addition of ketoesters to nitroolefins.

9. A process according to claim 7, wherein the reaction is a stereoselective addition of malonates to nitroolefins.

10. A process according to claim 7, wherein organic solvent of the reaction mixture of step (1) containing 2,2'-cyclopropylidene-bis(oxazoline) is selected from the group, consisting of hexane, benzene, toluene, chloroform, dichloromethane, dichloroethane, diethyl ether, methyl t-butyl ether and their mixtures.

11. A process according to claim 7, wherein the sorbent is silica gel.

12. A process according to claim 7, wherein for desorption an organic solvent is used, selected from the group, consisting of methanol, ethanol, n-propanol, isopropanol, acetone, methylethylketone, acetonitrile, tetrahydrofuran, 1,4-dioxane and their mixtures.

* * * * *